(12) United States Patent
Belpasso

(10) Patent No.: US 10,799,425 B2
(45) Date of Patent: Oct. 13, 2020

(54) ORAL HEALTH AID

(71) Applicant: Philip Ralph Belpasso, Fair Lawn, NJ (US)

(72) Inventor: Philip Ralph Belpasso, Fair Lawn, NJ (US)

(*) Notice: Subject to any disclaimer, the term of this patent is extended or adjusted under 35 U.S.C. 154(b) by 0 days.

(21) Appl. No.: 16/699,768

(22) Filed: Dec. 2, 2019

(65) Prior Publication Data
US 2020/0206085 A1    Jul. 2, 2020

Related U.S. Application Data

(63) Continuation-in-part of application No. 16/234,543, filed on Dec. 27, 2018.

(51) Int. Cl.
*A61J 7/00*    (2006.01)
*A61N 2/00*    (2006.01)
*A61N 1/05*    (2006.01)
*A61N 1/32*    (2006.01)
*A44C 9/00*    (2006.01)

(52) U.S. Cl.
CPC .......... *A61J 7/0092* (2013.01); *A44C 9/0069* (2013.01); *A61N 1/0548* (2013.01); *A61N 1/325* (2013.01); *A61N 2/002* (2013.01)

(58) Field of Classification Search
CPC .... A61J 7/0092; A44C 9/0069; A44C 9/0076; A44C 9/0061; A44C 15/007
See application file for complete search history.

(56) References Cited

U.S. PATENT DOCUMENTS 5,842,860 A * 12/1998 Funt ............... A61J 7/0092
                                                     433/80

OTHER PUBLICATIONS

Vintage Silver Dentures, sold Apr. 15, 2018 (https://www.etsy.com/listing/590134354/ vintage-silver-dentures-with-porcelain?show_sold_out_detail=1 accessed Oct. 4, 2019).*

* cited by examiner

*Primary Examiner* — Kortney L. Klinkel

(57) ABSTRACT

This invention is a oral health aid device to be places the user's mouth and maneuvered to cover their lower gum area at the teeth root line similar to chewing tobacco. The heath aid has on it a fastener, which can hold in place lozenges, which can contain flavors, or beneficially prescribed drugs, or antiviral and antibacterial antiseptic medication to satisfy the user's needs. This heath aid has been created because of the addiction-taking place recently by the now debunked electronic oil vaporing synthetic smoking devices. This health aid will help the young consumers who were extremely susceptible to anything related to oral fixation relief. Which in the case of very young people is a strong compulsion to use oral devices. This oral health aid will have in desired the ability to be reshaped into a finger ring. So it can be stored conveniently which the need for is exampled by the way baby pacifiers have a ring section attached.

9 Claims, 8 Drawing Sheets

ORAL HEALTH AID

The invention is an oral health aid comprising of a strip of material such as silver or copper which is cut to a length width and gauge so it can be bent easily to fit a person's mouth and maneuvered over their lower jaw to the teeth root level. The material which can in itself be an antiseptic to help control combat diseases. On the strip can be a fastener to hold in place a lozenge or holster for the administration of satisfying medications or desirer condiments. The wearing of the health aid will also satisfy the user's psychological oral fixation to have something in their mouth.

The fastener which can be used itself as a holster device or used to hold in place a cage to have put in it lozenge which can contain flavors, or beneficially prescribed drugs or antiviral and antibacterial antiseptic medication to satisfy the user's needs so the fastener device can be used for fastening in place cages and other holding apparatuses that can be used for the administration of treatments.

This health aid can come in two embodiments one is it being made of a malleable strip so that it can be uniquely reshaped from an oral health aid to and from a finger ring for storage when not used in the month. Or the oral health aid can be made in another embodiment a strip which is permanently shaped by copping a casting of the user's jaw shape including indentations to accommodate teeth roots being covered and having rounded edges on it circumference.

Also this oral health aid which is composed of a malleable or non-malleable strip of material bent to the shape of a person's jaw over the lower gum with an embedded fastener composed of a different metals from the strip characterized in as a dissimilar metal from the fastening device. In both embodiments of the malleable or non-malleable the strip and fastener will form a galvanic anode-cathode couple of electric potential inducing a current and electro-magnetic field to flow in the presence of saliva enhancing the direct antiseptic effect and the stimulation of immune response in the user.

BRIEF DESCRIPTION OF THE DRAWINGS

Reference is now made to the present illustrated in FIGS. 1-8.

Figure 1:
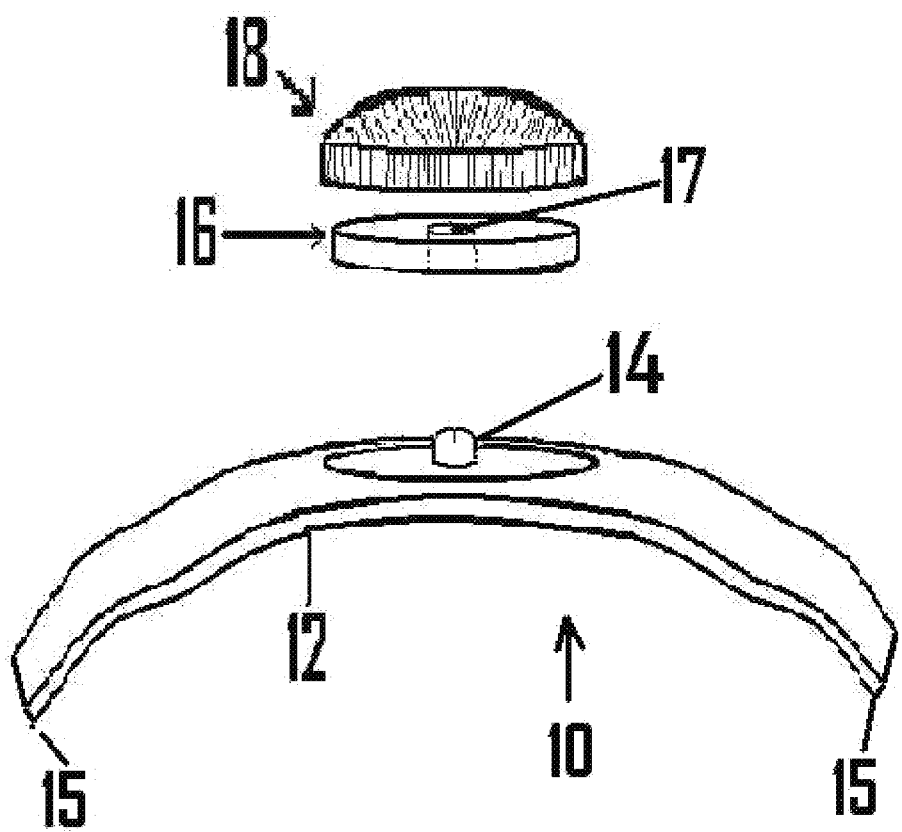
FIG. 1, Shows the Oral Health Aid 10 as a lower gum-covering device with the fastener 14 on it which can be used to fasten the lozenge 16 or a lozenge holding device 18.
Figure 2:
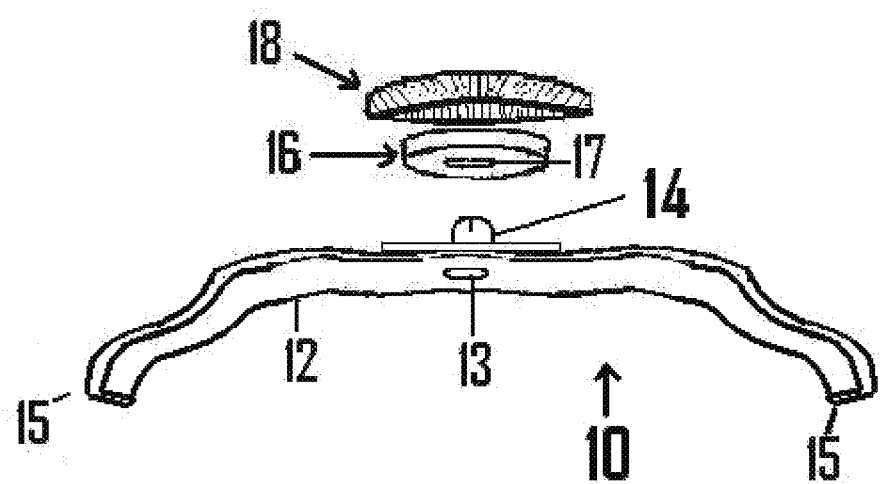
FIG. 2, Shows the Oral Health Aid 10 from the back side to reveal the screw's threads.
Figure 3:
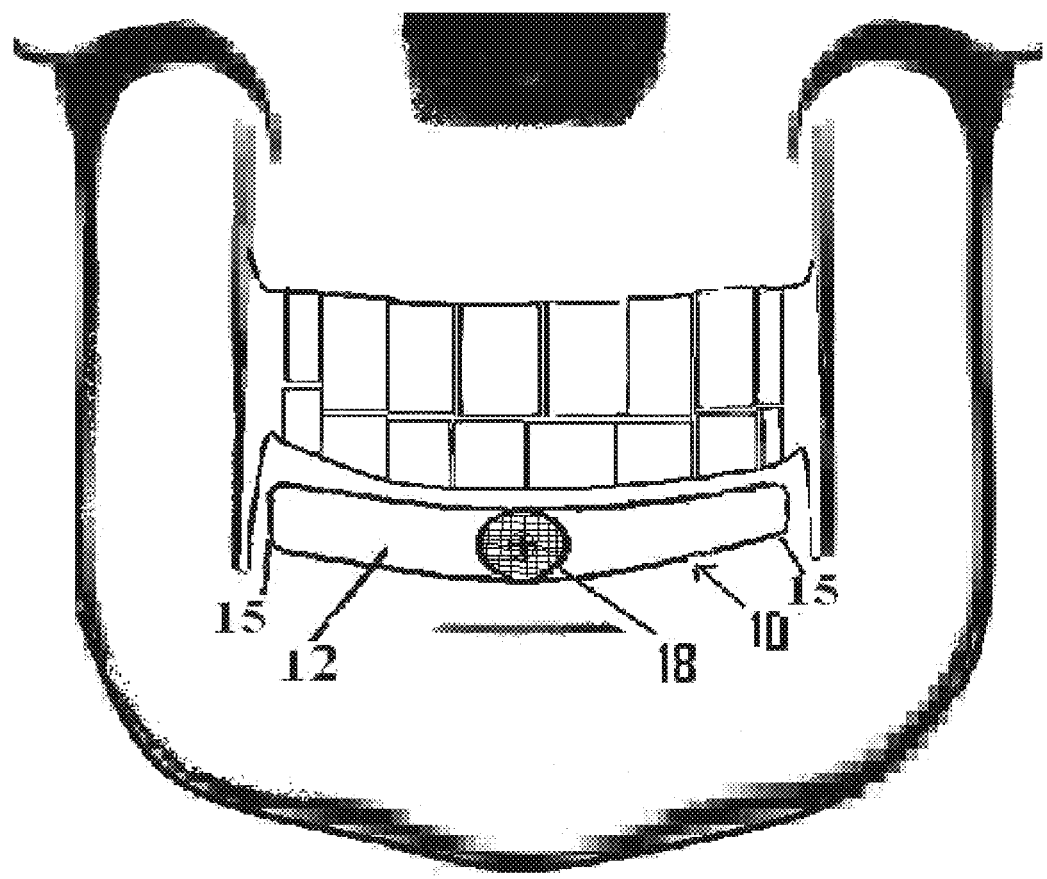
FIG. 3, is a closer look at Oral Health Aid 10 with its fastener 14 section and the lozenge 16 which is shown mounted which is held in place 17 in this instant a ball and socket along with pressure by the lower lip and the bottom gum.
Figure 4:
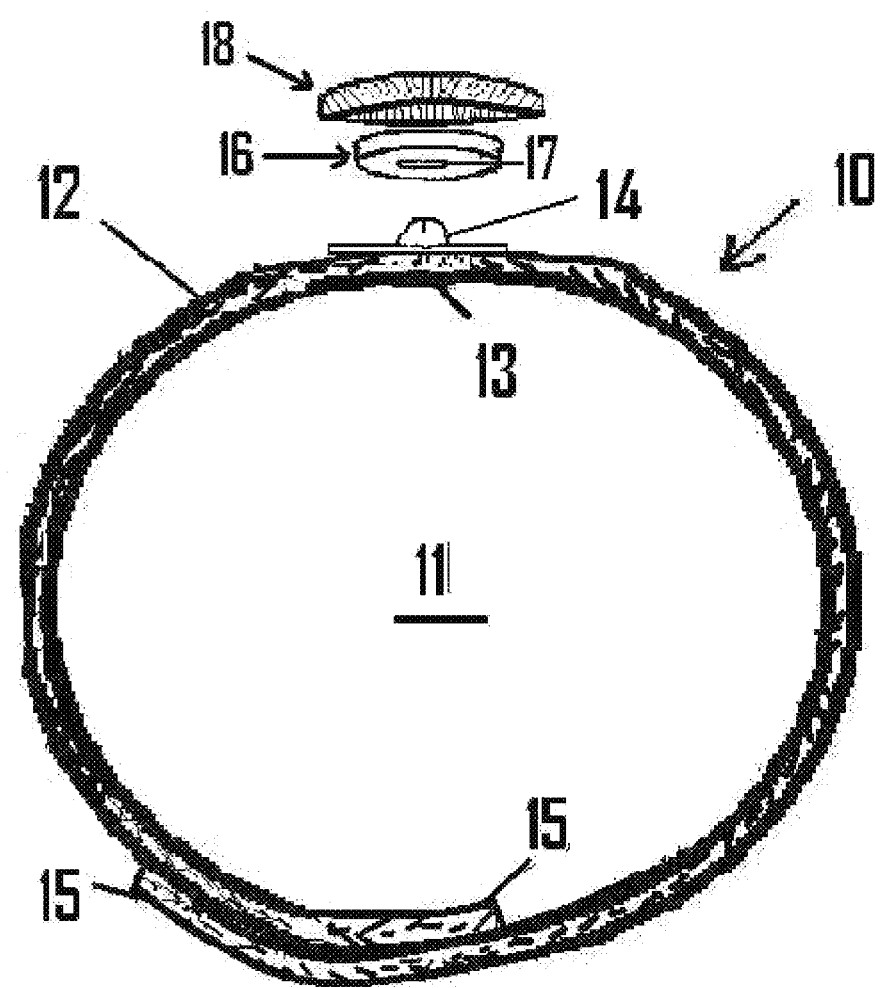
FIG. 4, is the Oral Health Aid 10 with its fastener 14 which will be fitted with the lozenge 16 which will have a receptor socket which is shown uncounted as it will not be called into play in this finger ring storage shape. By this reshaped oral health aid 10 it can then be stored by being worn as a finger ring by wrapping it around a finger which will result in its having an unusual over lapping to accommodate its jaw length with a fastener 14 to holed in place the lozenge 16 by way of a hole or crevice 17 or a holster device 18.

Notably the antiseptic material such as silver copper or gold and synthetics that if desired the non flexible to hold a shape of the lower jaw of the used, Or is can have the ability to shape changed so it can function as either a oral health aid or a finger ring in its rolled up shape it is a finger ring but can be unrolled with open ends 15, and made into a curved strip that can be inserted into the mouth and used as a health aid. The ring can have screwed into by way a hole 13 in its circumference a real Phillips head screw that is short in length so it can be mounted into the hole 13 and not interfere with the internal aperture of 11 when the ring is in its rolled up shape, or irritate the gum when used in its oral health aid state. The fastener 14 is optional as the health aid's function as an antiseptic however there is a important physiologically stimulate circulation by way of the cross on Phillip's head screw 14 which is representative of the positive attitude of the conscious mind over the bodies immune system which needs to be circulating to hard to reach places in the body such as outer skin and scare tissue.

The antiseptic material such as silver which makes up section 12 when in use as a ring will contain a passage 11 which must be unobstructed by 13 the coupling of the Phillips head screw 14 which has its top head pointing outward from the passage 11 of the rolled up ring shape 10.

FIG. 1 is a Philsring oral health aid, which has been reshaped from a finger ring by unrolling it so it can then be fitted in to the mouth of the user.

Figure 5:
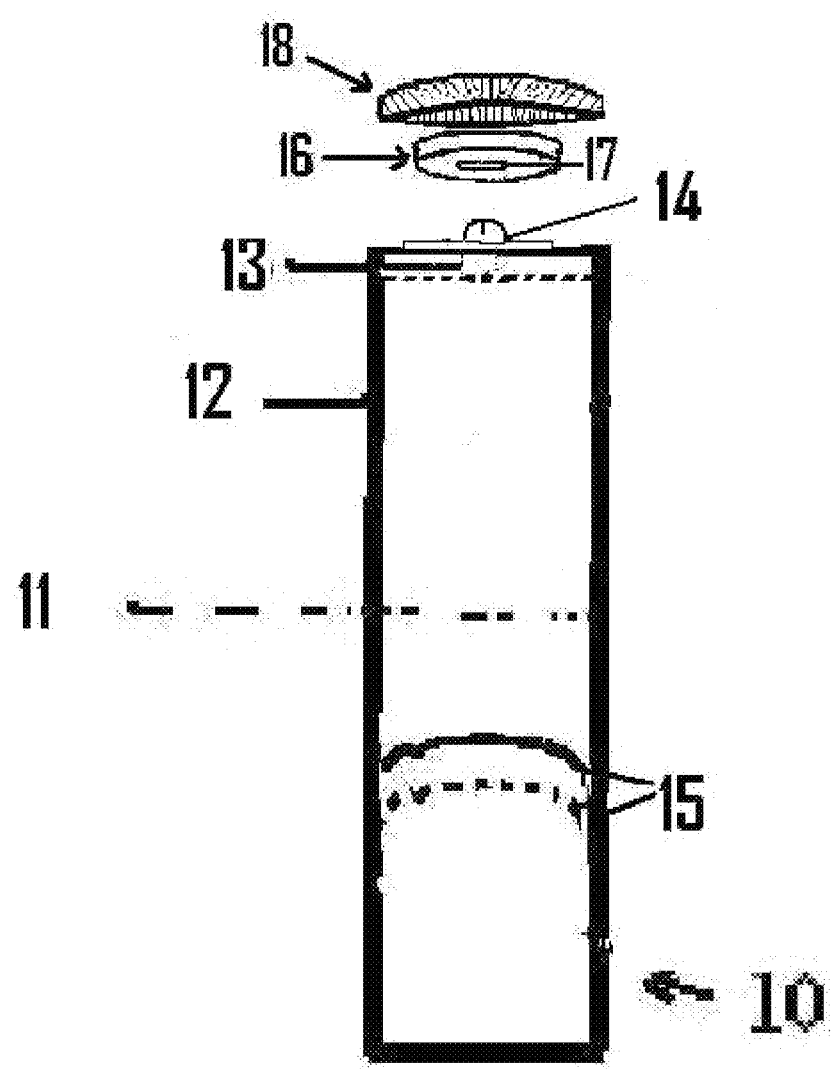
FIG. 5 is a side view of FIG. 4.
Figure 6:
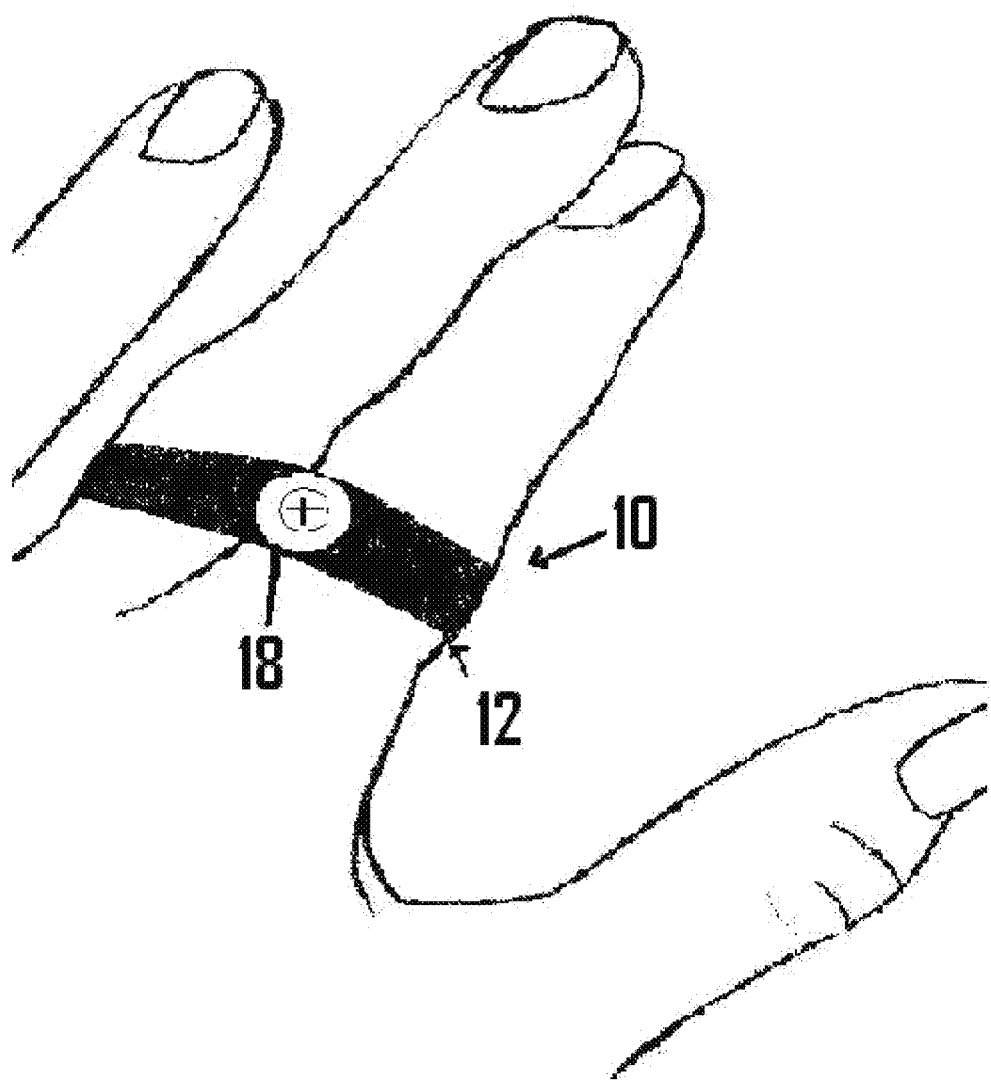
FIG. 6, is the Oral Health Aid 10 shaped as another style of being a two-finger ring to accommodate its jaw length with a fastener 14 to hold in place the lozenge 16 by way of a hole or crevice 17 or a holster device 18.
Figure 7:
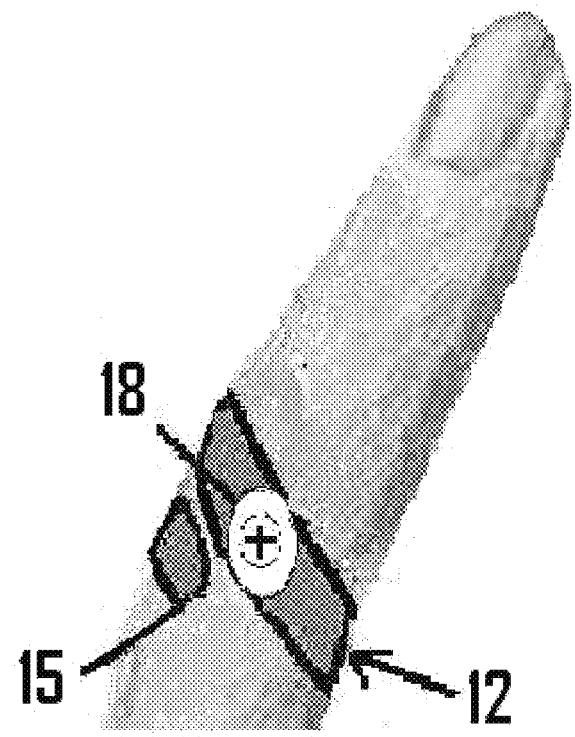
FIG. 7, is the Oral Health Aid 10 shaped as another style of finger ring as a spiral with two wrapping around a finger to accommodate its jaw length with a fastener 14 to holed in place the lozenge 16 by way of a hole or crevice 17 or a holster device 18.
Figure 8:
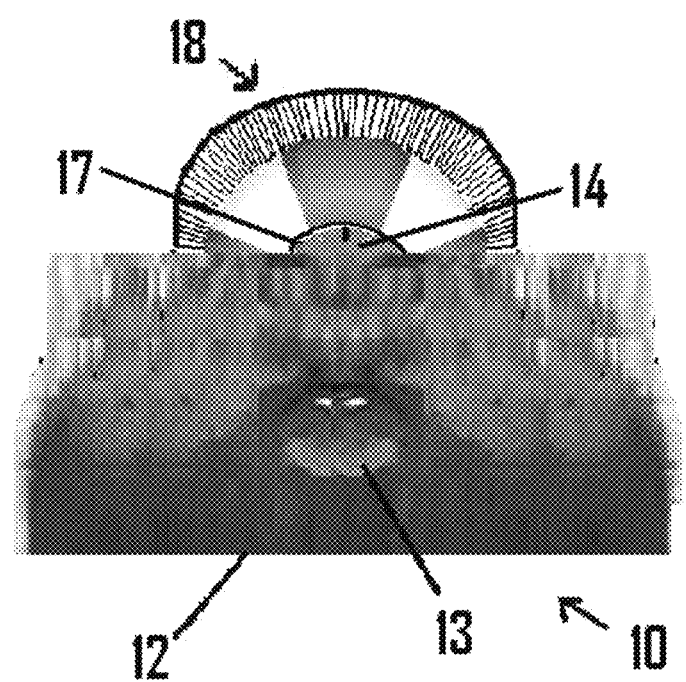
FIG. 8, is a photo of the back of the Oral Health Aid 10 which shows the threaded 13 part of the fastener 14 which can also be a rivet or welded or part of a casting to holed in place the lozenge 16 by way of a hole or crevice 17 or a holster device 18.

FIG. 5 is the fitted-oral health Aid showing its placement covering the lower jaw's gum area.

These embodiments are all primarily concerned with a new way of administering a beneficial sustenance to a person wearing the oral health aid however the health aid wearing also can effect both physical presents as well as a psychosomatic as a pacifier to satisfy the physiological need what is commonly known as oral obsession which if not confronted can result in extremely hazardous outward signs such as finger and nail biting, pencil knurling and other problems like nicotine addiction when cigarette smoking are used to quench the desire to have something in their mouth.

If the screw section 14 is made of stainless steal or aluminum which is different then the strip section 12 the continual change between wearer's body temperature via their pulse this two metal health aid will creates a dynamic electro magnetic stimulating the body. And if a real Philip-head screw 14 which can also be a torx star 14 which also has a religious positive mindfulness as a matter of it being the six pointed star both will of these health aid fastener will be enhanced by there tool design and also its unique three dimensional inverse shapes as the pyramid shape which is seen as floating with an illuminated eye on the back of the U.S. dollar. Or the six pointed star made by the thirteen five pointed stars which is over the eagle as also on the back of dollar in the in the Great Seal of the United States can have a similar positive mindful effect. However this fastener can be other many shapes which will function in the aforementioned way.

Simple stated this invention is oral health aid device which is characterized by its being for wearing in a person's mouth over their lower gum and can be reshaped if desired to be a ring which has a cut in its circumference to facilitated sizing and also enable easy taking off and putting on of the ring section which can be made of gold, silver or even copper which has a greening effect on the skin of the wearer which in effect creates a physiological change to the wearer. The mindful positive effect can also be further enhanced by the ring also having screwed through it a real screw in order to have the screw's threaded shaft come in contact with the wearer's skin a feature of the real fastener design.

The invention claimed is:

1. An oral health aid comprising a strip of material which is shaped to fit over the user's lower gums and having indentations to accommodate the user's teeth roots, wherein the shape is such that it does not cover the user's teeth when properly placed, wherein the strip has rounded edges on its circumference, wherein the oral health aid further comprises a device attached thereto to fasten in place a lozenge, wherein the lozenge includes a beneficial condiment, a beneficial drug, antiviral, antibacterial, and/or antiseptic medication.

2. The oral health aid of claim 1 wherein the strip is malleable such that it can be uniquely reshaped to form a finger ring which spirals around a finger or which can be shaped to be worn around two fingers for storage when not used in the mouth, and wherein the ring can be reshaped back into the strip that fits over the user's lower gums.

3. The oral health aid of claim 1 wherein the fastening device is a cage or other holding apparatus for administration of the lozenge.

4. The oral health aid of claim 1 wherein the aid further functions to satisfy the user's psychological oral fixation to have something in their mouth.

5. The oral health aid of claim 1 wherein the strip of material is silver, copper, or gold.

6. An oral health aid comprising a malleable or non-malleable strip of antiseptic metal which is shaped to fit over the user's lower gums and having indentations to accommodate the user's teeth roots, wherein the shape is such that it does not cover the user's teeth when properly placed, wherein the strip has rounded edges on its circumference wherein the oral health aid further comprises an embedded fastener made of a second metal different from the antiseptic metal of the strip characterized in that the second metal and the metal of the strip form a galvanic anode-cathode couple of electric potential including a current and electro-magnetic field to flow in the presence of saliva which enhances the direct antiseptic effect and stimulation of immune response in the user and wherein the embedded fastener is capable of holding a lozenge where the lozenge can be flavored and/or include a beneficial drug, antiviral, antibacterial, and/or antiseptic medication.

7. The oral health aid of claim 6 wherein the antiseptic strip is malleable such that it can be uniquely reshaped to form a finger ring which spirals around a finger or which can be shaped to be worn around two fingers for storage when not used in the mouth, and wherein the ring can be reshaped back into the strip that fits over the user's lower gums.

8. The oral health aid of claim 6 wherein the aid further functions to satisfy the user's psychological oral fixation to have something in their mouth.

9. The oral health aid of claim 6 wherein the strip of antiseptic metal is silver, copper, or gold.

* * * * *